United States Patent [19]

Ching et al.

[11] Patent Number: 5,189,190

[45] Date of Patent: Feb. 23, 1993

[54] VICINAL DISUBSTITUTED CARBOXYLIC ACIDS AND SILYLATED DERIVATIVES

[75] Inventors: Ta Y. Ching, Novato; Lon-Tang W. Lin, Vallejo, both of Calif.

[73] Assignee: Henkel Research Corporation, Santa Rosa, Calif.

[21] Appl. No.: 570,097

[22] Filed: Aug. 20, 1990

Related U.S. Application Data

[62] Division of Ser. No. 308,786, Feb. 8, 1989, Pat. No. 4,996,342.

[51] Int. Cl.$^5$ ............................. C07F 7/08; C07F 7/10
[52] U.S. Cl. ................................... 556/418; 556/413; 556/419; 556/437
[58] Field of Search ................ 556/437, 419, 413, 418

[56] References Cited

U.S. PATENT DOCUMENTS

| | | | |
|---|---|---|---|
| 4,315,825 | 2/1982 | Schweizer et al. | 252/41 |
| 4,578,504 | 3/1986 | Hammar | 556/437 X |
| 4,659,851 | 4/1987 | Plueddemann | 556/431 |
| 4,709,066 | 11/1987 | Chapman | 556/437 |
| 4,719,262 | 1/1988 | Plueddemann | 525/105 |
| 4,783,542 | 11/1988 | Chung | 556/437 |
| 4,785,126 | 11/1988 | Bruno | 556/437 X |
| 4,824,922 | 4/1989 | Chapman | 556/437 X |

*Primary Examiner*—Paul F. Shaver
*Attorney, Agent, or Firm*—Ernest G. Szoke; Wayne C. Jaeschke; John E. Drach

[57] ABSTRACT

Vicinal substituted $C_4$–$C_{24}$ carboxylic acid derivatives and their silane and siloxane derivatives as well as polymers and copolymers of silane and siloxane derivatives are disclosed. The compounds are useful as coupling agents, emulsifiers and demulsifiers, textile processing aids, and cosmetic additives.

15 Claims, No Drawings

VICINAL DISUBSTITUTED CARBOXYLIC ACIDS AND SILYLATED DERIVATIVES

This application is a divisional of 07/308,786, filed Feb. 8, 1989, and now U.S. Pat. No. 4,996,342.

BACKGROUND OF THE INVENTION

1. Field of the Invention

One aspect of this invention relates to novel vicinal substituted $C_4$-$C_{24}$ carboxylic acid derivatives, silane and siloxane derivatives thereof, and polymers and copolymers of silane and siloxane derivatives thereof.

2. Description of the Related Art

Organosilicon compounds are extremely useful materials. Simple organosilicon compounds such as alkylsilanes have been used as additives in such things as, paints, hydraulic fluids, heat transfer fluids, and dielectric fluids. Polymeric materials such as polysiloxanes have been used as defoamers, rubbers, coatings, and as additives in emulsions, greases, adhesives, and sealants. Most of these compounds contain silicon-oxygen and silicon-carbon bonds both of which contribute to the many unusual properties of these substances such as strong adhesion to smooth surfaces such as glass, thermal and oxidative stability, chemical these substances such as strong adhesion to smooth surfaces such as glass, thermal and oxidative stability, chemical inertness, resistance to weathering, and good dielectric strength. Because the presence of silicon-oxygen and carbon-silicon bonds contribute to the unique chemical and physical properties of organosilicon compounds, many methods of forming these types of bond have been developed over the years.

In the case of carbon-silicon bonds, one of the most widely used methods of forming them is through the addition of SiH bonds to carbon-carbon multiple bonds. This reaction, which is called hydrosilation or hydrosilylation, is well known in the art and has been used to make many types organsosilicon compounds. The reaction is usually carried out by reacting a substituted silane and a terminal alkene or terminal alkyne. These types of hydrosilylation reactions are normally initiated by heat, light, or radiation and catalyzed by peroxides, bases, and noble metal catalysts. The most widely used catalyst system is one involving chloroplatinic acid or some other platinum complex such as a platinum-olefin complex normally in a single phase system.

The compounds of the present invention can be made by reacting vicinal substituted $C_4$-$C_{24}$ carboxylic acids and functional derivatives thereof and trisubstituted silanes under standard hydrosilylation conditions similar to those described above. The novel vicinal substituted $C_4$-$C_{24}$ carboxylic acids and functional derivatives thereof of this invention contain an OH group vicinal to an ether group whose oxygen atom is bonded to the carbon chain of the carboxylic acid and a linear or branched alkenyl or alkynyl group having from 3 to 10 carbon atoms. Examples of such ether groups include —$OCH_2CH=CH_2$, —$OCH_2CH=CH$, and the like. Compounds similar to the novel vicinal substituted carboxylic acids and functional derivatives thereof of this invention have been described in U.S. Pat. No. 4,315,825. The patent discloses lithium salts of non-terminal vicinal substituted fatty acids having from 16 to 22 carbon atoms wherein the vicinal substituents are a hydroxy group and a group selected from the group consisting of alkoxy having from 2 to 18 carbon atoms, alkenoxy having from 3 to 18 carbon atoms. The patent does not disclose any functional derivatives of these fatty acids such as esters and amides or other metallic salts nor does it suggest that the claimed compounds could be used to make silylated derivatives. Compounds similar to the silane and siloxane derivatives of the novel vicinal substituted carboxylic acids and functional derivatives thereof have been described in U.S. Pat. Nos. 4,659,851 and 4,719,262. These patents disclose organosilicon compounds that contain a plurality of silicon-bonded alkoxy groups and at least one substituent that is bonded to silicon through oxygen and contains at least four carbon atoms two of which form a terminal group of the formula $CH_2=CH—$. None of the compounds of the present invention contain a substituent that is bonded to silicon through oxygen that also contains at least four carbon atoms two of which form a terminal group of the formula $CH_2=CH—$. It is an object of the present invention to provide novel carboxylic acid derivatives and hydrosilylated carboxylic acid derivatives useful as coupling agents, emulsifiers and demulsifiers, textile processing aids, and cosmetic additives.

DESCRIPTION OF THE INVENTION

Except for the operating examples, all numbers expressing quantities of ingredients or reaction conditions are understood to be modified by "about". Integers denoting the degree of polymerization in polymeric structures are understood to indicate the average degree of polymerization.

One aspect of the present invention relates to novel compounds of the formula

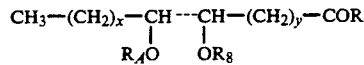

wherein R is: (a) OH; (b) an alkoxyl, or alkenoxyl group having from 1 to 6 carbon atoms; (c) a group having the formula $O(CH_2CH_2O)_a$—H wherein a is an integer having a value of from 1 to 20; (d) —$NR^2R^3$ wherein $R^2$ is H, $CH_3$, —$CH_2CH_3$, $CH_2CH_2OH$, —$CH_2CH_2N(CH_3)_2$, or —$(CH_2CH_2NH)_bH$ wherein b is an integer having a value of from 1 to 4, and $R^3$ is H, $CH_3$, —$CH_2CH_3$, —$CH_2CH_2OH$, —$CH_2CH_2N(CH_3)_2$; (e) $ON(R^9)_4$ wherein $R^9$ is hydrogen, —$CH_3$, —$CH_2CH_3$, —$CH_2CH_2OH$; $R_A$ is hydrogen, or a linear or branched aliphatic radical containing from 3 to 10 carbon atoms and having a double or triple bond; $R_B$ is hydrogen, or a linear or branched aliphatic radical containing from 3 to 10 carbon atoms and having a double or triple bond and with the proviso that either $R_A$ or $R_B$ are hydrogen; and wherein x is an integer having a value of from 0 to 10 and y is an integer having a value of from 0 to 10.

Another aspect of the present invention relates to novel compounds of the formula

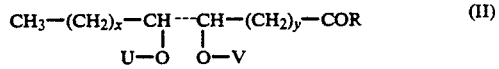

wherein R is: (a) OH; (b) OM wherein M is a metal ion selected from the group consisting of $Li^+$, $Na^+$, $K^+$, $Mg^{+2}$, $Ca^{+2}$, or $Ba^{+2}$; (c) an alkoxy, or alkenoxyl group having from 1 to 6 carbon atoms; (d) a polyethoxy group having the formula $O(CH_2CH_2O)_a$—H wherein a is an integer having a value of from 1 to 20;

(e) —NR$^2$R$^3$ wherein R$^2$ is H, CH$_3$, —CH$_2$CH$_3$, —CH$_2$CH$_2$OH, —CH$_2$CH$_2$N(CH$_3$)$_2$, or —(CH$_2$CH$_2$NH)$_b$H wherein b is an integer having a value of from 1 to 4, and R$^3$ is H, CH$_3$, —CH$_2$CH$_3$, —CH$_2$CH$_2$OH, —CH$_2$CH$_2$N(CH$_3$)$_2$; (f) ON(R$^9$)$_4$ wherein R$^9$ is hydrogen, —CH$_3$, —CH$_2$CH$_3$, —CH$_2$CH$_2$OH; U is hydrogen, or G—R$_c$ wherein G is a bivalent radical derived from a linear or branched alkane or alkene having from 3 to 10 carbon atoms; R$_c$ is (a) Si(OR$^5$)$_3$ wherein R$^5$ is an alkyl group having from 1 to 4 carbon atoms or (b) Si(R$^6$)$_3$ wherein R$^6$ is an alkyl group having from 1 to 3 carbon atoms; V is hydrogen, or G—R$_c$ wherein G is a bivalent radical derived from an linear or branched alkane or alkene having from 3 to 10 carbon atoms; R$_c$ is (a) Si(OR$^5$)$_3$ wherein R$^5$ is an alkyl group having from 1 to 4 carbon atoms or (b) Si(R$^6$)$_3$ wherein R$^6$ is an alkyl group having from 1 to 3 carbon atoms, with the proviso that U or V is hydrogen; and wherein x is an integer having a value of from 0 to 10 and y is an integer having a value of from 0 to 10;

Another aspect of the present invention relates to novel polymeric compounds of the formula $$CH_3-(CH_2)_x-\underset{\underset{J-O}{|}}{CH}-\underset{\underset{O-K}{|}}{CH}-(CH_2)_y-COR \quad (III)$$

wherein R is: (a) OH; (b) OM wherein M is a metal ion selected from the group consisting of Li$^+$, Na$^+$, K$^+$, Mg$^{+2}$, Ca$^{+2}$, or Ba$^{+2}$; (c) an alkoxyl, or alkenoxyl group having from 1 to 6 carbon atoms, (d) a polyethoxy group having the formula O(CH$_2$CH$_2$O)$_a$—H wherein a is an integer having a value of from 1 to 20, (e) —NR$^2$R$^3$ wherein R$^2$ is H, CH$_3$, —CH$_2$CH$_3$, —CH$_2$CH$_2$OH, —CH$_2$CH$_2$N(CH$_3$)$_2$, or —(CH$_2$CH$_2$NH)$_b$H wherein b is an integer having a value of from 1 to 4, and R$^3$ is H, CH$_3$, —CH$_2$CH$_3$, —CH$_2$CH$_2$OH, —CH$_2$CH$_2$N(CH$_3$)$_2$; (f) ON(R$^9$)$_4$ wherein R$^9$ is hydrogen, —CH$_3$, —CH$_2$CH$_3$, —CH$_2$CH$_2$OH; J is hydrogen, or G—R$_D$ wherein G is a bivalent radical derived from an linear or branched alkane or alkene having from 3 to 10 carbon atoms, K is hydrogen, or G—R$_D$ wherein G is a bivalent radical derived from an linear or branched alkane or alkene having from 3 to 10 carbon atoms with the proviso that J or K is hydrogen; and R$_D$ is

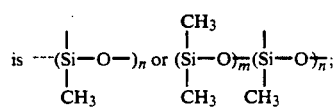

wherein x is an integer having a value of from 0 to 10 and y is an integer having a value of from 0 to 10; m and n are integers having values such that m/n has a value of from 0 to 30 and m+n is equal to or less than 300.

The first group of compounds of the present invention are made by reacting epoxidized carboxylic acids or functional derivatives thereof with unsaturated alcohols to form alkenyloxy- or alkynyloxy-substituted carboxylic acids. The second group of compounds of the present invention are made by reacting the alkenyloxy- or alkynyloxy-substituted carboxylic acids or functional derivatives thereof with simple trisubstituted silanes to form the siloxane derivatives of the alkenyloxy- or alkynyloxy-substituted carboxylic acids. The third group of compounds of the present invention are made by reacting the alkenyloxy- or alkynyloxy-substituted carboxylic acids or functional derivatives thereof with polymeric trisubstituted silanes to form the siloxane derivatives of the alkenyloxy- or alkynyloxy-substituted carboxylic acids. For example, a representative member of the first group of compounds of the present invention can be prepared by reacting methyl 9,10-epoxyoctadecanoate with allyl alcohol and acid catalyst such as sulfuric acid to form methyl 9,10 (or 10,9)-hydroxyallyloxyoctadecanoate (A) as depicted in Eq.I.

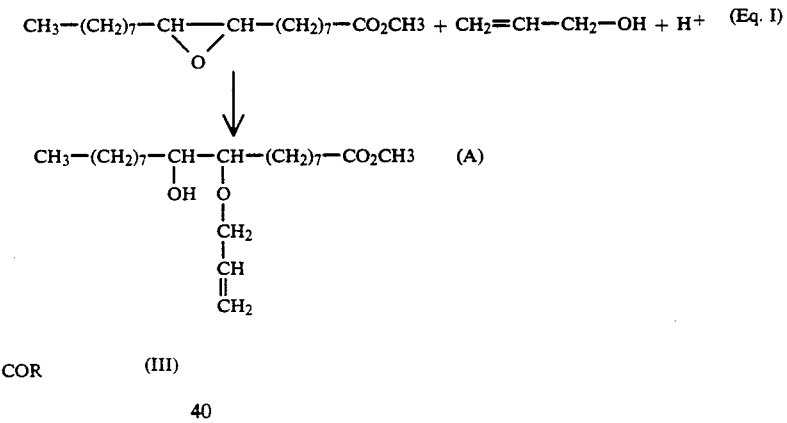

A representative member of the second group of compounds of the present invention can be made by reacting Compound A, the alkenyloxy derivative of methyl oleate, with a trisubstituted silane, for example trimethoxysilane to form a hydrosilated derivative, a compound of the present invention as depicted in (Eq. II)

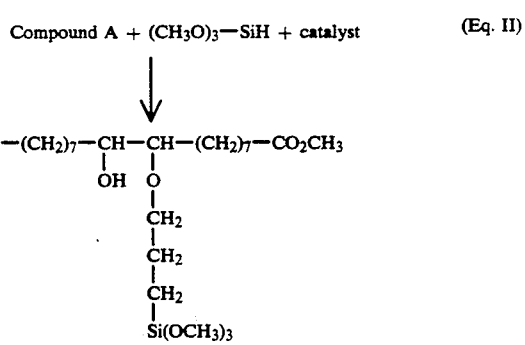

A representative member of the third group of compounds of the present invention can be made by reacting Compound A with a polymeric trisubstituted silane, for example polymethylhydrosiloxane to form a polymeric derivative, Compound C, as depicted in Eq. III.

(Eq. III)
Compound A + copolymer of polymethylhydrosiloaxane and polymethylsiloxane

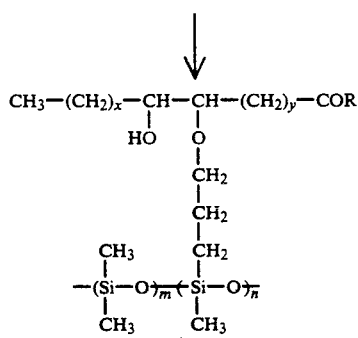

Any unsaturated alcohol having a carbon-carbon double or triple bond and having from 3 to 10 carbon atoms can be used to make the compounds of the present invention. Alcohols having a carbon-carbon double bond include 2-propen-1-ol, 3-butene-1-ol, 3-butene-2-ol, 1-penten-3-ol, 2-penten-1-ol, 3-penten-2-ol, 4-penten-1-ol, 4-penten-2-ol, 1-hexen-3-ol, 2-hexen-1-ol, 4-hexen-1-ol, 5-hexen-1-ol, 1-hepten-3-ol, 1-octen-3-ol, cis-3-nonen-1-ol, and 9-decen-1-ol. Alcohols having a carbon-carbon triple bond include 2-propyn-1-ol, 2-butyn-1-ol, 3-butyn-1-ol, 1-pentyn-3-ol, 3-pentyn-1-ol, 3-hexyn-1-ol, 1-octyn-3-ol, 3-nonyn-1-ol, and 3-decyn-1-ol. The most preferred alcohol is 2-propen-1-ol.

Any carboxylic acid, ester, or amide having an epoxide functionality in its carbon chain can be used to make compounds of formula I. These epoxidized acids, esters, or amides are usually made by epoxidizing unsaturated acids, esters, or amides through any of the known epoxidation methods such as reaction with m-chloroperoxybenzoic acid. The preferred carboxylic acids are naturally occurring unsaturated fatty acids such as undecylenic acid (9-undecenoic acid), oleic acid (cis-9-octadecenoic acid), elaidic acid (trans-9-octadecenoic acid), palmitoleic acid (9-hexadecenoic acid), and erucic acid (cis-13-docosenoic acid) or their esters or amides.

The most preferred epoxidized carboxylic acid is epoxidized oleic acid, 9,10-epoxyoctadecanoic acid or any of its esters or amides. Any epoxidized carboxylic acid, salt, ester, or amide having an epoxide functionality in its carbon chain can be used to make compounds of formula II and III. The preferred compounds are naturally occurring epoxidized unsaturated fatty acids such as epoxidized undecylenic acid (9-undecenoic acid), epoxidized oleic acid (cis-9-octadecenoic acid), epoxidized elaidic acid (trans-9-octadecenoic acid), epoxidized palmitoleic acid (9-hexadecenoic acid), and epoxidized erucic acid (cis-13-docosenoic acid) or the salts, esters or amides thereof. Any simple trialkyl silane having from 1 to 4 carbon atoms may be used to make compounds of formula II including trimethyl silane, triethyl silane, tripropyl silane, and tributyl silane. Any trialkoxy silane having from 1 to 3 carbon atoms may be used to make the compounds of formula II including trimethoxy silane, triethoxy silane, tripropoxy silane, and tributoxy silane.

Any polymeric trisubstituted silane may be used to make the compounds formula III. The preferred polymeric trisubstituted silanes are polymethylhydridosiloxane and copolymers of methylhydridosiloxane and dimethylsiloxane.

In one group of preferred compounds of general formula I, R is $OCH_3$, $x=y=7$, $R_A$ is $-CH_2CH=CH_2$, and $R_B$ is hydrogen (or the isomeric compound wherein $R_A$ is hydrogen, and $R_B$ is $-CH_2CH=CH_2$); R is $-CH_2CH=CH_2$, $x=y=7$, $R_A$ is $-CH_2CH=CH$, and $R_B$ is hydrogen (or the isomeric compound wherein $R_A$ is hydrogen, and $R_B$ is $-CH_2CH=CH_2$); R is $-O(CH_2CH_2O)_2-H$, $x=y=7$, $R_A$ is $-CH_2CH=CH$, and $R_B$ is hydrogen (or the isomeric compound wherein $R_A$ is hydrogen, and $R_B$ is $-CH_2CH=CH_2$).

In one group of preferred compounds of the general formula II, R is $OCH_3$, $x=y=7$, U is hydrogen, V is $G-R_C$ wherein G is $-CH_2CH_2CH_2-$, and $R_C$ is Si-$(OCH_3)_3$ (or the isomeric compound thereof wherein V is hydrogen, U is $G-R_C$ wherein G is $-CH_2CH_2CH_2-$, and $R_C$ is $Si(OCH_3)_3$); R is $OCH_3$, $x=y=7$, U is hydrogen, V is $G-R_C$ wherein G is $-CH_2CH_2CH_2-$, and $R_C$ is $Si(OCH_2CH_3)_3$ (or the isomeric compound thereof wherein V is hydrogen, U is $G-R_C$ wherein G is $-CH_2CH_2CH_2-$, and $R_C$ is $Si(OCH_2CH_3)_3$); R is $-O(CH_2CH_2O)_2-H$, U is hydrogen, V is $G-R_C$ wherein G is $-CH_2CH_2CH_2-$, and $R_C$ is $Si(OCH_3)_3$ (or the isomeric compound thereof wherein V is hydrogen, U is $G-R_C$ wherein G is $-CH_2CH_2CH_2-$, and $R_C$ is $Si(OCH_3)_3$); R is OH, U is hydrogen, V is $G-R_C$ wherein G is $-CH_2CH_2CH_2-$, and $R_C$ is Si-$(OCH_2CH_3)_3$ (or the isomeric compound thereof wherein V is hydrogen, U is $G-R_C$ wherein G is $-CH_2CH_2CH_2-$, and $R_C$ is $Si(OCH_2CH_3)_3$); R is $-ONH_4$, U is hydrogen, V is $G-R_C$ wherein G is $-CH_2CH_2CH_2-$ and $R_C$ is $Si(OCH_2CH_3)_3$ (or the isomeric compound thereof wherein V is hydrogen, U is $G-R_C$ wherein G is $-CH_2CH_2CH_2-$, and $R_C$ is $Si(OCH_2CH_3)_3$); R is ONa, U is hydrogen, V is $G-R_C$ wherein G is $-CH_2CH_2CH_2-$ and $R_C$ is Si-$(OCH_2CH_3)_3$ (or the isomeric compound thereof wherein V is hydrogen, U is $G-R_C$ wherein G is $-CH_2CH_2CH_2-$, and $R_C$ is $Si(OCH_2CH_3)_3$); R is OK, U is hydrogen, V is $G-R_C$ wherein G is $-CH_2CH_2C-H_2-$, and $R_C$ is $Si(OCH_2CH_3)_3$ (or the isomeric compound thereof wherein V is hydrogen, U is $G-R_C$ wherein G is $-CH_2CH_2CH_2-$, and $R_C$ is Si-$(OCH_2CH_3)_3$).

In one group of preferred compounds of general formula III, R is $OCH_3$, J is hydrogen, K is $G-R_D$ wherein G is $-CH_2CH_2CH_2$, 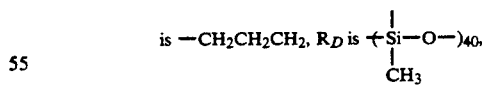

(or the isomeric compound thereof wherein K is hydrogen, J is $G-R_D$ wherein G is $-CH_2CH_2CH_2-$, 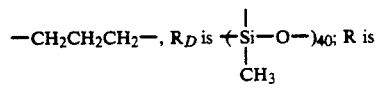 R is

J is hydrogen, K is $G-R_D$ wherein G is $-CH_2CH_2CH_2$, $R_D$ is 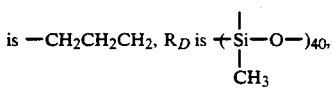

(or the isomeric compound thereof wherein K is hydrogen, J is G—$R_D$ wherein G is

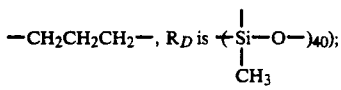

R is $OCH_3$, J is hydrogen, K is G—$R_D$ wherein G is $-CH_2CH_2CH_2-$,

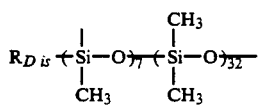

(or the isomeric compound thereof wherein K is hydrogen, J is G—$R_D$ wherein G $-CH_2CH_2CH_2-$,

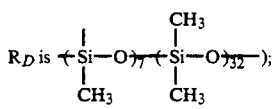

R is $-NHCH_2CH_2N(CH_3)_2$, J is hydrogen, K is G—$R_D$ wherein G is $CH_2CH_2CH_2-$,

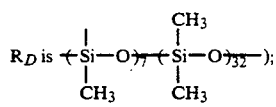

(or the isomeric compound thereof wherein K is hydrogen, J is G—$R_D$ wherein G $-CH_2CH_2CH_2-$,

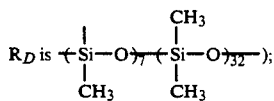

R is $-(CH_2CH_2O)_2-H$, J is hydrogen, K is G—$R_D$ wherein G $-CH_2CH_2CH_2-$,

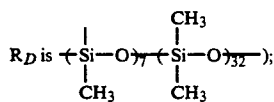

(or the isomeric compound thereof wherein K is hydrogen, J is G—$R_D$ wherein G $-CH_2CH_2CH_2-$,

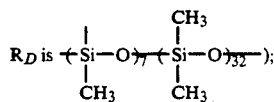

The following examples are meant to illustrate but not limit the invention.

EXAMPLE 1

Preparation of methyl 9,10 (or 10,9)-hydroxyallyloxyoctadecanoate

Approximately 19.0 grams of methyl 9,10-epoxyoctadecanoate (85% purity) (0.052 moles), 35.0 grams of allyl alcohol (0.61 moles) and 0.04 grams of concentrated sulfuric acid were heated to 60° C. for 6 hours. The reaction mixture was then stirred with about 1.0 grams of ion exchange resin IRA-93. The resin was filtered off and the unreacted allyl alcohol was stripped under vacuum. A 76% yield of a product characterized by I.R. and NMR spectral analysis was obtained.

EXAMPLE 2

Preparation of allyl 9,10 (or 10,9)-hydroxyallyloxyoctadecanoate.

Approximately 31.4 grams of methyl 9,10-epoxyoctadecanoate (85% purity) (0.086 moles), 56.0 grams of allyl alcohol (0.98 moles) and 0.5 grams of cocnentrated sulfuric acid were heated to 60° C. for 6 hours. The reaction mixture was then stirred with about 1.0 grams of ion exchange resin IRA-93. The resin was filtered off and the unreacted allyl alcohol was stripped under vacuum.

The products were methyl 9,10 (or 10,9)-hydroxyallyloxyoctadecanoate (75% yield) and allyl 9,10 (or 10,9)-hydroxyallyloxyoctadecanoate (15% yield).

EXAMPLE 3

Preparation of 9,10 (or 10,9)-hydroxyallyloxyoctadecanoic acid.

Approximately 37.0 grams of the product from example 1 (0.085 moles) and 8.4 grams of potassium hydroxide (0.15 moles) in 50 grams of ethanol were heated to reflux for 6 hours. Two thirds of the solvent was removed and 300 grams of water were added. The solution was acidified with 15.0 grams of sulfuric acid. The acid was extracted twice with 100 grams of ether. The combined organic layers were dried over magnesium sulfate. The ether was stripped to give the product in a 95% yield.

EXAMPLE 4

Preparation of 2-(2-hydroxyethyloxy)ethyl-9,10 (or 10.9)-hydroxyallyloxyoctadecanoate.

Approximately 35.6 grams (0.13 moles) of the product from example 3 and 30.0 grams of diethylene glycol [2(2-hydroxyethyl)ethanol] (0.28 moles) in 50 grams of benzene containing 0.1 grams of toluenesulfonic acid were heated to reflux for 8 hours. Water was removed by a water trap. The mixture was washed with a sodium chloride solution and water. The organic layer was dried over magnesium sulfate, and the benzene removed to give the product in a 90% yield.

EXAMPLE 5

Preparation of N-(N',N-'dimethylaminoethyl) 9,10 (or 10,9)-hydroxyallyloxyoctadecanamide.

Approximately 37.0 grams of the product from example 1 (0.085 moles) 27.0 grams of N,N-dimethylethylenediame (0.31 moles) were heated to 150° C. under pressure for 8 hours. Unreacted amine was stripped to give the product in a 95% yield.

EXAMPLE 6

Preparation of methyl 9-(3-triethoxysilylpropoxy)-10-hydroxy (or 10,9)octadecanoate.

A mixture of about 37.0 grams of the product from example 1 (0.10 moles) and about 16.4 grams of triethoxysilane was dissolved in about 50.0 grams of toluene. One third of this solution was placed in a 3-neck flask equipped with a condenser, an addition funnel and a thermometer. The solution was heated to 45° C. and a toluene solution containing about 0.2 grams of platinum divinyltetramethyldisiloxane was added to intiate the hydrosilylation. The rest of the solution was then slowly added and the temperature was maintained at 70° C. After 4 hours at this temperature, the solution was cooled and about 2.0 grams of activated charcoal was added. The solids were filtered and the solvent was stripped to give the product which was characterized by I.R., NMR and mass spectral analysis. The product yield was 95%.

EXAMPLE 7

Preparation of poly [methyl-9,10-allyloxyhydroxy (or 10,9) octadecanoate] methylsiloxane.

The procedure of example 6 was repeated except that about 6.1 grams of polymethylhydrosiloxane were used in place of the 16.4 grams of triethoxysilane. The yield of product was about 90%.

EXAMPLE 8

Preparation of a copolymer of methyl 9-(3-trisilylpropoxy)-10-hydroxy (or 10,9) octadecanoatemethylsiloxane and dimethylsiloxane.

The procedure of example 6 was repeated except that about 85.0 grams of copolymethylhydrosiloxanedimethylsiloxane were used in place of the 16.4 grams of triethoxysilane. The yield of product was about 90%.

EXAMPLE 9

Preparation of poly [N-triethylenetriamine 9-(3-trisilylpropoxy-10-hydroxy (or 10,9) octadecanamide] methylsiloxane.

About 4.3 grams of the product from example 7 were mixed with about 7.5 grams of triethylenetetraamine (TETA) and heated to 150° C. for 5 hours. The unreacted amine was extracted with about 80.0 grams of ether to give an oil which was characterized by I.R., NMR and mass spectral analysis to be the desired product. The yield was about 65%.

EXAMPLE 10

Preparation of 2-(2-hydroxyethyloxy)ethyl-9-(3-triethoxysilylpropoxy)-10-hydroxy (or 10,9) octadecanoate.

The procedure of example 6 was repeated except that approximately 44.0 grams of the product of example 4 and approximately 17.0 grams of triethoxysilane in 80 grams of benzene were used. The product yield was about 90%.

EXAMPLE 11

Preparation of a copolymer of N-triethylenetriamine 9-(3-trisilylpropoxy-10-hydroxy (or 10,9) octadecanamide methylsiloxane and dimethylsiloxane.

Approximately 8.5 grams of the product from example 8 were mixed with 7.0 grams of triethylenetriamine and the mixture was heated to 150° C. for 3 hours. The mixture was quenched with water to precipitate an oil which later was extracted with methylene chloride after the water was removed. The organic layer was dried over magnesium sulfate and the solvent was removed to give an oil which was characterized to be the product. The yield was 90%.

EXAMPLE 12

Preparation of poly [N-(N',N'dimethylaminoethyl)-9,10 (or 10,9)-hydroxyallyloxyoctadecanamide] methylsiloxane.

Approximately 4.3 grams of product from example 7 were mixed with 1.8 grams of N,N-dimethyethylenediame amd 0.04 grams of sodium methoxide at 150° C. under pressure for 18 hours (till the ester peak disappeared in the I.R.). The mixture was extracted with methylene chloride and inorganic salt was filtered off. The solvent was stripped to give an oil which was characterized to be the product. The yield was 91%.

EXAMPLE 13

Preparation of a copolymer of N-(N',N'dimethylaminoethyl)-9,10 (or 10,9)-hydroxyallyloxyoctadecanamide] methylsiloxane and dimethylsiloxane.

Approximately 4.3 grams of the product from example 8 were mixed with 1.8 grams of N,N-dimethyethylenediame and 0.04 grams of sodium methoxide at 150° C. under pressure for 18 hours (till the ester peak disappeared in the I.R.). The mixture was extracted with methylene chloride and inorganic salt was filtered off. The solvent was stripped to give an oil which was characterized to be the product. The yield was 90%.

EXAMPLE 14

Preparation of poly [9,10 (or 10,9)-hydroxyallyloxyoctadecanoic acid] methylsiloxane.

Approximately 37.0 grams of the product from example 7 (0.085 moles) and 8.4 grams of potassium hydroxide (0.15 moles) in 50 grams of ethanol were heated to reflux for 6 hours. Two thirds of the solvent was removed and 300 grams of water were added. The solution was acidified with 5.0 grams of sulfuric acid. The acid was extracted twice with 100 grams of ether. The combined organic layers were dried over magnesium sulfate. The ether was stripped to give the product in a 90% yield.

EXAMPLE 15

Preparation of 9-(3-triethoxysilylpropoxy-10-hydroxy (or 10,9) octadecanoic acid.

The procedure of example 6 was repeated except that 35.6 grams of the product from example 3 and 16.4 grams of triethoxysilane in 80 grams of benzene were used. The yield was 95%.

We claim:

1. A compound of the formula

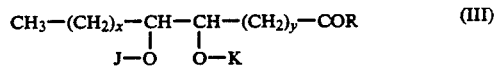

(III)

wherein R is: (a) OH; (b) OM wherein M is a metal ion selected from the group consisting of $Na^+$, $K^+$, $Mg^{+2}$, $Ca^{+2}$, or $Ba^{+2}$; (c) an alkoxyl, or alkenoxyl group having from 1 to 6 carbon atoms; (d) a polyethoxy group having the formula $O(CH_2CH_2O)_a$—H wherein a is an integer having a value of from 1 to 20; (e) —$NR^2R$ wherein $R^2$ is H, —$CH_3$, —$CH_2CH_3$, —$CH_2CH_2OH$, —$CH_2CH_2N(CH_3)_2$, or —$(CH_2CH_2NH)_bH$ wherein b is an integer having a value of from 1 to 4, and $R^3$ is H, $CH_3$, —$CH_2CH_3$, —$CH_2CH_2OH$, —$CH_2CH_2N(CH_3)_2$; (f) $ON(R^9)_4$ wherein $R^9$ is hydrogen, —$CH_3$, —CH$_2$CH$_3$, —CH$_2$CH$_2$OH; J is hydrogen, G—R$_D$ wherein G is a bivalent radical derived from an linear or branched alkane or alkene having from 3 to 10 carbon atoms, K hydrogen, G—R$_D$ wherein G is a bivalent radical derived from an linear or branched alkane or alkene having from 3 to 10 carbon atoms with the proviso that only one of J or K is hydrogen; and R$_D$ is

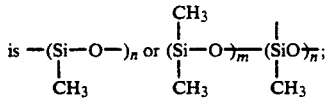

wherein x is an integer having a value of from 0 to 10 and y is an integer having a value of from 0 to 10; m and n are integers having values such that m/n has a value of from 0 to 30 and m+n is equal to or less than 300.

2. A compound of claim 1 wherein R is OCH$_3$, J is hydrogen,

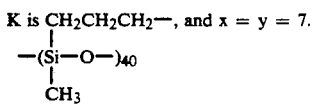

3. A compound of claim 1 wherein R is OCH$_3$, K is hydrogen,

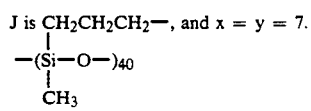

4. A compound of claim 1 wherein R is —ON(CH$_3$)$_4$, J is hydrogen,

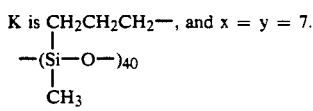

5. A compound of claim 1 wherein R is —ON(CH$_3$)$_4$, J is hydrogen,

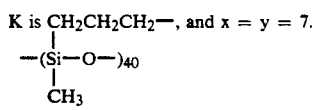

6. A compound of claim 1 wherein R is —NH(CH$_2$CH$_2$NH)$_3$—H, J is hydrogen,

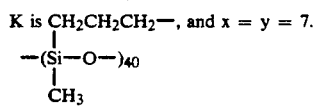

7. A compound of claim 1 wherein R is —NH(CH$_2$CH$_2$NH)$_3$—H, K is hydrogen,

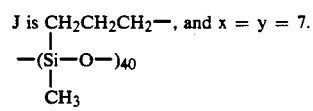

8. A compound of claim 1 wherein R is NH(CH$_2$CH$_2$NH)$_3$, J is hydrogen,

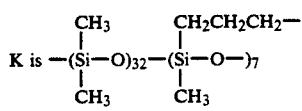

and x=y=7.

9. A compound of claim 1 wherein R is —NH(CH$_2$CH$_2$NH)$_3$—H, K is hydrogen,

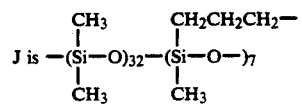

and x=y=7.

10. A compound of claim 1 wherein R is O(CH$_2$CH$_2$O)$_2$—H, J is hydrogen,

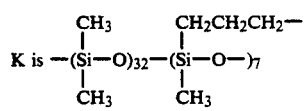

and x=y=7.

11. A compound of claim 1 wherein R is O(CH$_2$CH$_2$O)$_2$—H, K is hydrogen,

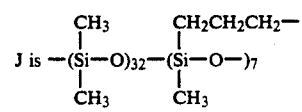

and x=y=7.

12. A compound of claim 1 wherein R is NH(CH$_2$CH$_2$N(CH$_3$)$_2$, J is hydrogen,

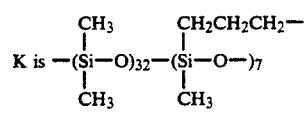

and x=y=7.

13. A compound of claim 1 wherein R is NH(CH$_2$CH$_2$N(CH$_3$)$_2$, K is hydrogen,

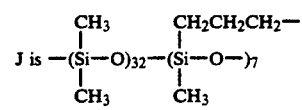

and x=y=7.

14. A compound of claim 1 wherein R is OCH$_3$, J is hydrogen,

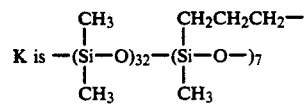

and x=y=7.

15. A compound of the formula

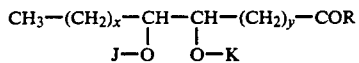 (III)

wherein R is: (a) OH; (b) OM wherein M is a metal ion selected from the group consisting of Na+, K+, Mg+2, Ca+2, or Ba+2; (c) an alkoxyl, or alkenoxyl group having from 1 to 6 carbon atoms; (d) a polyethoxy group having the formula $O(CH_2CH_2O)_a$—H wherein a is an integer having a value of from 1 to 20; (e) —$NR^2R$ wherein $R^2$ is H, —$CH_3$, —$CH_2CH_3$, —$CH_2CH_2OH$, —$CH_2CH_2N(CH_3)_2$, or —$(CH_2CH_2NH)_bH$ wherein b is an integer having a value of from 1 to 4, and $R^3$ is H, $CH_3$, —$CH_2CH_3$, —$CH_2CH_2OH$, —$CH_2CH_2N(CH_3)_2$; (f) $ON(R^9)_4$ wherein $R^9$ is hydrogen, —$CH_3$, —$CH_2CH_3$, —$CH_2CH_2OH$; J is hydrogen; K is G—$R_D$ wherein G is a bivalent radical derived from an linear or branched alkane or alkene having from 3 to 10 carbon atoms with the proviso that only one of J or K is hydrogen; and $R_D$ is

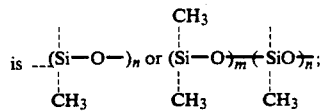

wherein x is an integer having a value of from 0 to 10 and y is an integer having a value of from 0 to 10; m and n are integers having values such that m/n has a value of from 0 to 30 and m+n is equal to or less than 300.

* * * * *